United States Patent [19]
Subramaniam et al.

[11] Patent Number: 5,710,356
[45] Date of Patent: Jan. 20, 1998

[54] METHOD OF CONDUCTING AN ENDOTHERMIC REACTION IN A PACKED-BED REACTOR WITH EXTERNAL ENERGY ADDITION

[75] Inventors: Bala Subramaniam; Jon D. Snyder, both of Lawrence, Kans.

[73] Assignee: The University of Kansas, Lawrence, Kans.

[21] Appl. No.: 343,218

[22] Filed: Nov. 22, 1994

[51] Int. Cl.⁶ .................................................... C07C 5/32
[52] U.S. Cl. ...................... 585/440; 585/441; 585/910; 208/166; 208/169
[58] Field of Search .................. 208/166, 174, 208/169, 165; 585/440, 441, 910

[56] References Cited

U.S. PATENT DOCUMENTS

| | | | |
|---|---|---|---|
| 3,839,197 | 10/1974 | Greenwood et al. | 208/174 |
| 3,865,927 | 2/1975 | Watson | 423/570 |
| 3,882,015 | 5/1975 | Carson | 208/169 |
| 4,039,650 | 8/1977 | Daley | 423/569 |
| 4,229,603 | 10/1980 | Lyon | 585/444 |
| 4,478,808 | 10/1984 | Matros et al. | 423/522 |
| 4,725,416 | 2/1988 | Kristof et al. | 423/239 |
| 4,778,826 | 10/1988 | Jezl et al. | 518/703 |
| 4,836,988 | 6/1989 | Kristof et al. | 422/171 |
| 4,877,592 | 10/1989 | Matros et al. | 423/245.1 |
| 5,053,572 | 10/1991 | Kim et al. | 585/441 |
| 5,080,872 | 1/1992 | Jezl et al. | 422/201 |
| 5,188,804 | 2/1993 | Pace et al. | 422/111 |
| 5,304,698 | 4/1994 | Husain . | |

OTHER PUBLICATIONS

Snyder, Jon D. et al.; "Flow Reversal Operation of Packed-Bed Reactors: Application to Endothermic Reactions"; Submitted to AICHE Journal on microfiche only Oct. 1993.

*Primary Examiner*—Glenn A. Caldarola
*Assistant Examiner*—Bekir L. Yildirim
*Attorney, Agent, or Firm*—Hovey, Williams, Timmons & Collins

[57] ABSTRACT

A novel, packed-bed, reverse flow reactor is provided for the endothermic dehydrogenation of ethylbenzene to styrene. The catalyst bed is flanked by inert end sections to prevent the occurrence of the reverse reaction. Ethylbenzene vapor is added at one end of the reactor while superheated steam is added concurrently at a downstream location. The flow direction is periodically reversed by alternating the ethylbenzene introduction between the reactor ends and the steam introduction between axially symmetric locations away from the reactor ends. Employing a steam to ethylbenzene feed ratio of 8:1 to 10.2:1 (as compared to 12:1 to 17:1 employed during conventional adiabatic operation), it is shown that the proposed reverse flow operation produces reactor temperatures that are hundreds of degrees higher than the mixing cup temperature of the feed streams. While catalyst temperatures are at a maximum when the steam is introduced midway between the reactor ends, splitting the steam addition among multiple axially symmetric locations produces lower and more uniform temperatures that are better suited to providing optimum ethylbenzene conversion and styrene selectivity while maintaining efficient utilization of the added energy.

21 Claims, 7 Drawing Sheets

METHOD OF CONDUCTING AN ENDOTHERMIC REACTION IN A PACKED-BED REACTOR WITH EXTERNAL ENERGY ADDITION

BACKGROUND OF THE INVENTION

For solid-catalyzed, mildly exothermic reactions in packed-bed reactors, it has been well established in recent years that periodic reverse flow operation can significantly reduce energy requirements as compared to conventional operation using unidirectional flow (Boreskov et al. 1983; Boreskov and Matros, 1983; Matros, 1989). Periodic reverse flow operation efficiently traps the enthalpy of reaction in the reactor bed which functions as a regenerative heat exchanger. As discussed in the referenced investigations, the relatively cool feed gases are heated by the inlet portion of the bed to sufficiently high temperatures to provide fast reaction rates. The hot product gases heat the outlet portion of the bed. Upon flow reversal, the cycle is continued. After a sufficient number of flow reversals, a stationary state characterized by a bell-shaped temperature profile is attained.

The average capacity of ethylbenzene dehydrogenation plants is over 100,000 metric tons per year (Sundaram et al., 1991). Hence, small improvements in plant operation efficiency can lead to relatively large returns. The subject of ethylbenzene dehydrogenation has been reviewed in detail elsewhere (Lee, 1973). The reaction is highly endothermic, the adiabatic temperature drop for complete conversion of pure ethylbenzene to styrene from an initial temperature of 910 K being roughly 580 K. However, total conversion is impractical because styrene formation is limited kinetically and thermodynamically at lower temperatures. During adiabatic reactor operation, steam is usually mixed with the ethylbenzene feed in order to maintain reactor temperatures at which reasonably high reaction rates are realized. Molar steam to ethylbenzene ratios of 15 to 20 are noted in the literature (Carra and Forni, 1965; Sheel and Crowe, 1969; Modell, 1972). The resulting high flow rates can lead to large pressure drops across tubular flow reactors (Rase, 1990).

Reflecting on the energy related expenses affecting the plant economics, Sheel and Crowe (1969) noted that the plant from which they obtained their kinetic data could be operated more efficiently using a steam to hydrocarbon ratio of 17. However, the throughput was limited by the product condenser capacity and the plant was forced to employ a lower ratio of roughly 13. Although higher temperatures achieved with steam addition favors the equilibrium conversion to styrene, side reactions become significant at higher reactor temperatures. Hence optimum feed temperatures are usually sought to achieve desirable styrene selectivity while maintaining relatively high ethylbenzene conversions. A feed temperature value of 900 K is typical for conventional operation (Carra and Forni, 1965; Sheel and Crowe, 1969; Modell, 1972).

Short (1985) discusses an isothermal process for producing styrene that employs steam/ethylbenzene ratios of roughly seven and a feed temperature of 850 K. The lower steam/ethylbenzene ratios are claimed to result in substantial savings in cooling and separation costs. However, the isothermal process requires a relatively complex setup to provide for countercurrent flow of molten salt around the reactor tube bank. Haynes et al. (1992) proposed a quasi-flow reversal reactor operation for carrying out the endothermic dehydrogenation of ethylbenzene using twin reactor beds. By alternatively heating one of the two reactors with steam flowing from one end, then introducing ethylbenzene from the other, Haynes et al. exploited regenerative heat exchange to maintain a monotonically increasing temperature profile in the reactor bed thereby inhibiting the reverse reaction.

U.S. Pat. Nos. 3,865,927 and 4,478,808 to Watson and Matros et al., respectively, disclose methods which use a periodic reverse flow reactor to carry out the exothermic oxidation reaction of sulfur dioxide. While the methods may be effective in carrying out exothermic reactions, they are not practical for endothermic reactions. Continuous endothermic reactions carried out by use of the methods disclosed in the '927 or '808 patents would result in the reaction quenching itself due to a lack of heat necessary to drive the endothermic reaction. Thus, the '927 and '808 patents neither teach nor suggest the introduction of heat from an external source into the reactor catalyst bed. Further, the mere addition of heat to the center of a catalyst bed, without proper temperature profiling, could produce undesirable results, such as catalyst overheating, catalyst coking, undesired by-product formation, and inefficient energy utilization.

Accordingly, the requirements for the economical production of styrene are exceedingly stringent, with the most troublesome difficulty being to maximize the utilization of added energy while optimizing styrene selectivity.

SUMMARY OF THE INVENTION

The present invention overcomes the problems outlined above, and provides an improved process for the conversion of ethylbenzene to styrene. The invention is predicated on the discovery that a periodic reverse flow strategy may be employed in a single catalyst bed reactor in which steam is introduced at discrete axially symmetric positions to develop temperature profiles which are known to favor desired product selectivity and conversion, but with significantly less energy.

In the case of production of styrene from ethylbenzene, steam is introduced at axially symmetric interior positions. Concurrent introduction of a fraction of the steam at interior positions, instead of adding all the steam along with the ethylbenzene at a reactor end, is intended to take advantage of not only regenerative heat exchange, but also energy trapping in the reactor bed. The flow direction of the combined streams is periodically reversed by alternating the ethylbenzene/steam feed between the reactor ends and the steam introduction between axially symmetric positions. This results in a peak-shaped axial temperature profile at stationary state. While the hotter central portion of the reactor bed favors styrene formation, the reverse reaction is thermodynamically favored at the cooler reactor ends. This problem is circumvented by employing catalytically inert packing material at the reactor ends. The inert packing material also functions as a regenerative heat exchange medium.

DETAILED DESCRIPTION OF THE PREFERRED EMBODIMENTS

The following examples set forth preferred techniques and compositions, as well as simulated and actual test results demonstrating the maximization of energy utilization and the extent to which styrene selectivity can be optimized.

Periodic flow reversal is the cyclic switching of the direction of flow in a fixed bed reactor by alternating the feed introduction between the ends of the reactor. For endothermic reactions, reverse flow operation, together with the addition of energy at interior reactor locations (rather than at the reactor ends), traps the heat of reaction in the central portion of the reactor. During reverse flow operation, a peak shaped temperature profile develops and continually moves to the left and right with each flow reversal. The cool inlet gases are heated by the inlet section of the bed to sufficiently high temperatures to cause fast reaction rates. The hot product gases then heat the outlet section of the bed. Thus, periodic flow reversal permits the use of feed temperatures well below those which would extinguish a reaction during conventional operation. After a sufficient number of flow reversals, a stationary state is attained such that the spatiotemporal temperature and concentration profiles during a given semicycle converge upon single solutions that are invariant during succeeding flow reversals.

For the endothermic dehydrogenation of ethylbenzene to styrene, it is desirable to distribute a given amount of energy among the interior locations in such a way that overtemperatures are avoided and a desired catalyst bed temperature profile is attained. Presented in the examples (see FIGS. 11–14) are results of experimental investigations aimed at understanding the effects of operating parameters such as total energy input, energy introduction locations, and semicycle period on energy trapping and bed temperature profiles during discrete energy introduction.

EXAMPLE 1

A mathematical model of the proposed reverse flow scheme of the instant invention is disclosed in this example.

The model is solved numerically to elucidate the effects of steam temperature, the steam entry location(s), and the length of the inert sections on the energy trapping characteristics, ethylbenzene product selectivity. Using a relatively low feed steam/ethylbenzene ration of eight (as compared to 12–17 employed during conventional adiabatic unidirectional operation), it is shown that the reverse flow strategy of the instant invention can produce reactor temperatures that are hundreds of degrees greater than the mixing cup temperature of the combined feed streams. Further, it is shown that near-isothermal operation at desirable catalyst temperatures (about 900 K) is possible when the steam addition among several axially symmetric locations.

Model Development

Figures 1, 2:
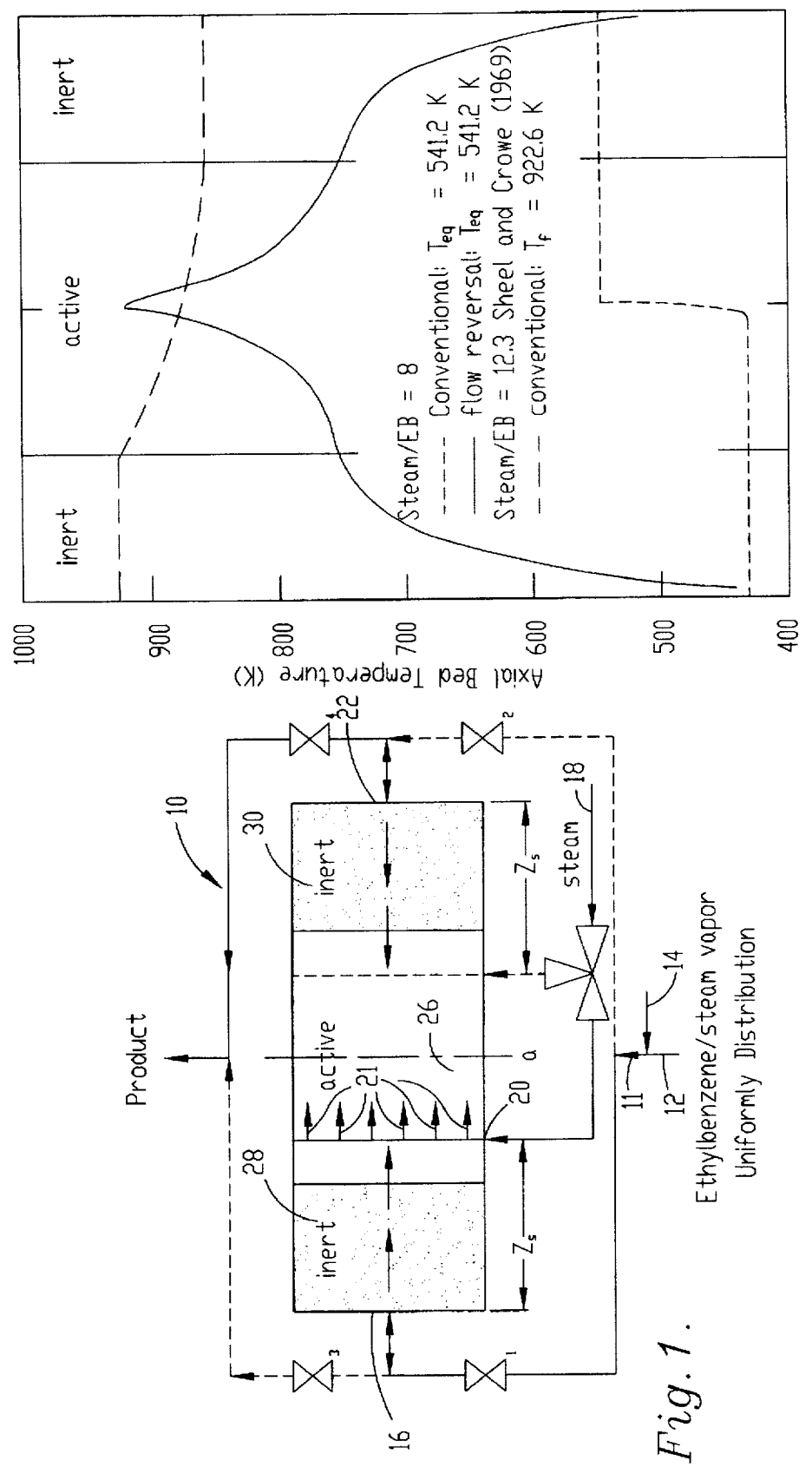
FIG. 1 is a schematic of a reverse flow reactor for the catalytic dehydrogenation of ethylbenzene to styrene with a portion of the steam added in a secondary stream at axially symmetric locations.
FIG. 2 is a comparison of axial bed temperature profiles attained during reverse flow operation to those attained during conventional operation.

A one-dimensional, heterogeneous fixed-bed reactor model was developed to simulate the performance of an adiabatic reverse flow reactor for ethylbenzene dehydrogenation on a Shell-105 catalyst. FIG. 1 is a schematic of the proposed reverse flow reactor 10 having axial center shown by line "a" in FIG. 1. Ethylbenzene vapor 12 mixed with steam 14 (at molar steam/ethylbenzene ratio of 6:1) and mixture 11 is introduced at a first reactor end 16 while additional steam 18 is introduced concurrently at a reactor downstream position 20 (for a total molar steam\ethylbenzene ratio of 8:1), creating a combined stream 21 within reactor 10. Although steam addition at interior locations rather than at the ends favors energy trapping and provides better energy utilization, steam presence over the catalyst is necessary to mitigate catalyst coking and maintain its oxidation state (sometimes referred to herein as "catalyst activity"). A steam/ethylbenzene ratio of 6:1 is in the lower range of values employed during conventional isothermal unidirectional operation.

In the flow scheme of the instant invention, the flow direction of flow of the combined streams 21 is periodically reversed by alternating the steam+ethylbenzene mixture 11 so that it is introduced at a second reactor end 22 and the additional steam 18 is introduced at a second position 24 which is axially symmetric to positions 20. The catalyst bed 26 is flanked by inert end sections 28 and 30 which serve as the regenerative heat exchange medium and prevent the occurrence of the reverse reactions at the cooler reactor ends.

In addition to styrene formation, undesired side reactions that produce benzene, toluene, ethylene, and methane are also included in the model. The model accounts for density variations in the gas phase reaction mixture, incorporates correlations based on temperature and flow conditions to calculate the local interpellet heat transfer coefficients, and employs temperature and composition dependent gas phase heat capacities. Implicit in the model development are the following assumptions:

1. Steam is uniformly mixed with the hydrocarbon stream at the steam entry locations. (Other embodiments of the invention may include non-uniform steam mixing).
2. The gases behave ideally at the low pressures and high temperatures of the reactor.
3. Pressure drop across the reactor bed is neglected as being small at the flow rates used.
4. The heat capacity of the catalyst bed is assumed to be constant.
5. Axial mass dispersion is characterized by an effective dispersion coefficient which varies with velocity.
6. As justified in Appendix B, axial heat conduction is described by an effective conductivity term in the gas phase.

7. Radial temperature gradients are considered negligible during adiabatic reactor operation. (Alternative embodiments may include operations where radial temperature gradients exist.)
8. For reasons explained elsewhere (Snyder and Subramaniam, 1993), pseudo steady state rate expressions are employed.
9. The rate expressions employed in our simulations are adopted from Sheel and Crowe (1969). Implicit is the assumption that transport limitations, if any, are accounted for in the rate expressions. The various reactions considered in the model and the corresponding rate expressions are given in Appendix A.
10. Intrapellet temperature gradients are considered to be insignificant.

A transient material balance for the $i^{th}$ component in the reactor gas phase yields:

$$\epsilon \frac{\partial(y_i \cdot C)}{\partial t} = -\frac{\partial(G_T \cdot y_i)}{\partial z} + \frac{\partial}{\partial z}\left(D_{ez} \cdot C \frac{\partial y_i}{\partial z}\right) + R_i \quad (1)$$

Five independent reactor material balances for ethylbenzene, styrene, hydrogen, toluene, and benzene yield unique solutions for the axial mole fraction profiles of all the species in the system.

The total molar flux at an axial position is determined by the molar fluxes of the feed streams and by the change in the molar flux due to reaction. Considering that there is a net increase of one mole for every mole of styrene or benzene formed, the change in the total molar flux due to the occurrence of reactions in the active portion of the reactor bed is given by $$G_T = \Sigma G_f + \int_0^z (r_1 + r_2) dz \quad (2)$$

where the integral term represents the change in the molar flux due to reaction. Clearly, the reaction rate terms are in the inert end sections.

A transient energy balance for the reactor gas phase is as follows:

$$\epsilon \frac{\partial(h_g \cdot C)}{\partial t} = -\frac{\partial(G_T \cdot h_g)}{\partial z} + \frac{\partial}{\partial z}\left(D_{ez} \cdot C \frac{\partial h_g}{\partial z}\right) + \quad (3)$$

$$\frac{\partial}{\partial z}\left(k'_{ez} \cdot G_T \frac{\partial T_g}{\partial z}\right) + h_h \cdot a \cdot (T_p - T_g)$$

Equation (3) assumes a point source term for the enthalpy of the steam addition. The accumulation term is expressed as follows as a function of the temperature and composition.

$$\frac{\partial(h_g \cdot C)}{\partial t} = \frac{P}{R_g}\left(\frac{\partial \frac{h_g}{T_g}}{\partial T_g} \frac{\partial T_g}{\partial t} + \Sigma \frac{\partial \frac{h_g}{T_g}}{\partial y_i} \frac{\partial y_i}{\partial t}\right). \quad (4)$$

Expressing the accumulation term in this manner improves the numerical stability of the solution by providing the temperature profile of the previous time step as the reference for the new time step.

The second term on the right hand side of Eq. (3) represents the axial dispersion of energy due to the axial dispersion of species with different enthalpies. For a system in which the material balance includes an effective mass dispersion term and the energy balance incorporates composition dependent heat capacities, an energy dispersion term resulting from the mass dispersion of species with different enthalpies is also required. Details of this formulation are presented in Appendix B.

The initial temperature and mole fraction profiles are either assumed or are known. The boundary conditions associated with the reactor material and energy balances (Eqs. 1 and 3) are as follows:

$$D_{ez} \cdot C \frac{\partial y_i}{\partial z} = G_T(y_i - y_{i,f}) \quad \text{at } z = 0 \quad (5)$$

$$\frac{\partial y_i}{\partial z} = 0 \quad \text{at } z = L \quad (6)$$

$$D_{ez} \cdot C \frac{\partial h_g}{\partial z} + k'_{ez} \cdot G_T \frac{\partial T_g}{\partial z} = G_T(h_h - h_{g,f}) \quad \text{at } z = 0 \quad (7)$$

$$\frac{\partial h_g}{\partial z} = 0 \quad \text{at } z = L \quad (8)$$

It should be noted that Eqs. (5–8) are steady state boundary conditions. The use of Eq. (8) is justified because the velocity of the reactant mixture downstream of the steam entry location is such that relatively small temperature gradients occur downstream of the reactor bed shortly after each flow reversal. Furthermore, past reactor exit (where there is no packing), the effective axial thermal conductivity becomes insignificant.

Assuming a value of two for the axial mass dispersion Peclet number (Froment, 1967) yields:

$$D_{ez} \cdot C = r_p \cdot G_T \quad (9)$$

Incorporating the relationship provided by Eq. (9), Eq. (7) was further simplified to provide numerical stability at the zeroth node by approximating the heat capacity at the entrance to the heat capacity of the feed.

$$r_p \cdot c_{pf} \frac{\partial T_g}{\partial z} + k'_{ez} \frac{\partial T_g}{\partial z} = c_{pf} \cdot (T_g - T_{g,f}) \quad (10)$$

The energy balance for the pellet phase is as follows:

$$\rho_p \cdot C_{p,p} \frac{\partial T_p}{\partial t} = h_h \cdot \frac{a}{(1-\epsilon)} \cdot (T_g - T_p) - \frac{\sum_{j=1}^{3} \eta_j \cdot \Delta H_{R,j}}{(1-\epsilon)} \quad (11)$$

Correlations for the local external heat transport coefficients are taken from Yoshida et al. (1962).

The physicochemical and operating parameters used in the simulations are summarized in Table 1. The pure component enthalpies are calculated by integrating the heat capacity equations to the temperatures of interest in 0.1 K increments. The pure component enthalpy derivatives with respect to temperature, and the reaction rate constants are similarly calculated. These precalculated values are assigned to arrays for efficient access. During each iteration, a subroutine calculates the mixture enthalpy and enthalpy derivative terms at all spatial nodes using the appropriate values of the gas mole fractions and temperatures.

The model is solved numerically using a combination of techniques. The partial differential equations representing the material and energy balances for the reactor void (Eqs. 1, 3) are discretized using a backward difference approximation for the flow terms, and a centered-in-space approximation for the other spatial and temporal derivative terms. Appendix C provides an example of the finite difference approximation for a second derivative term at a steam entry location. The numerical simulation incorporates 247 spatial nodes, except where otherwise noted, and a time step of 0.1 second. The resulting tridiagonal matrices for the gas phase material and energy balance equations are solved using an iterative formulation of the Thomas technique (Bruce et al., 1953). The energy balance equation for the catalyst pellet (Eq. 11) is solved using an implicit finite difference formulation. The equations representing the energy balances are coupled through the heat transfer terms. The material and energy balance equations for the gas phase are coupled through the enthalpy and reaction terms. All equations are solved iteratively until convergence is reached at each time step.

The numerical simulations were performed on a VAX 7000 computer. Approximately five seconds of CPU time were required for computing the temperature profiles associated with one flow reversal. The total number of flow reversals to attain a stationary state typically ranged between 200 and 400, depending on the proximity of the chosen initial conditions to the final stationary state and on the reactor temperatures. It was found that simulations incorporating 83 nodes required approximately two seconds of CPU time per flow reversal and yielded quantitatively similar results in the central region of the reactor, but produced greater numerical dispersion at the ends of the reactor, due primarily to the use of a backward difference approximation for the flow terms.

Results

Reverse flow reactor performance for carrying out the endothermic dehydrogenation of ethylbenzene is evaluated using the following measures: the maximum bed temperature, the space average bed temperature and the space average catalyst section temperature immediately prior to flow reversal at stationary state; and the time average ethylbenzene conversions and selectivity during a semicycle period at stationary state. The semicycle period is defined as the time duration between successive flow reversals. The axial temperature and conversion profiles presented in the figures pertain to the stationary state immediately prior to flow reversal with flow occurring from the left to the right. The equivalent mixed feed temperature, defined as the mixing cup temperature of the feed streams at the specified flow rates and temperatures, is employed as a measure of the amount of energy introduced into the reactor.

Comparison of Flow Reversal Operation with Unidirectional Flow Operation

Figure 3:
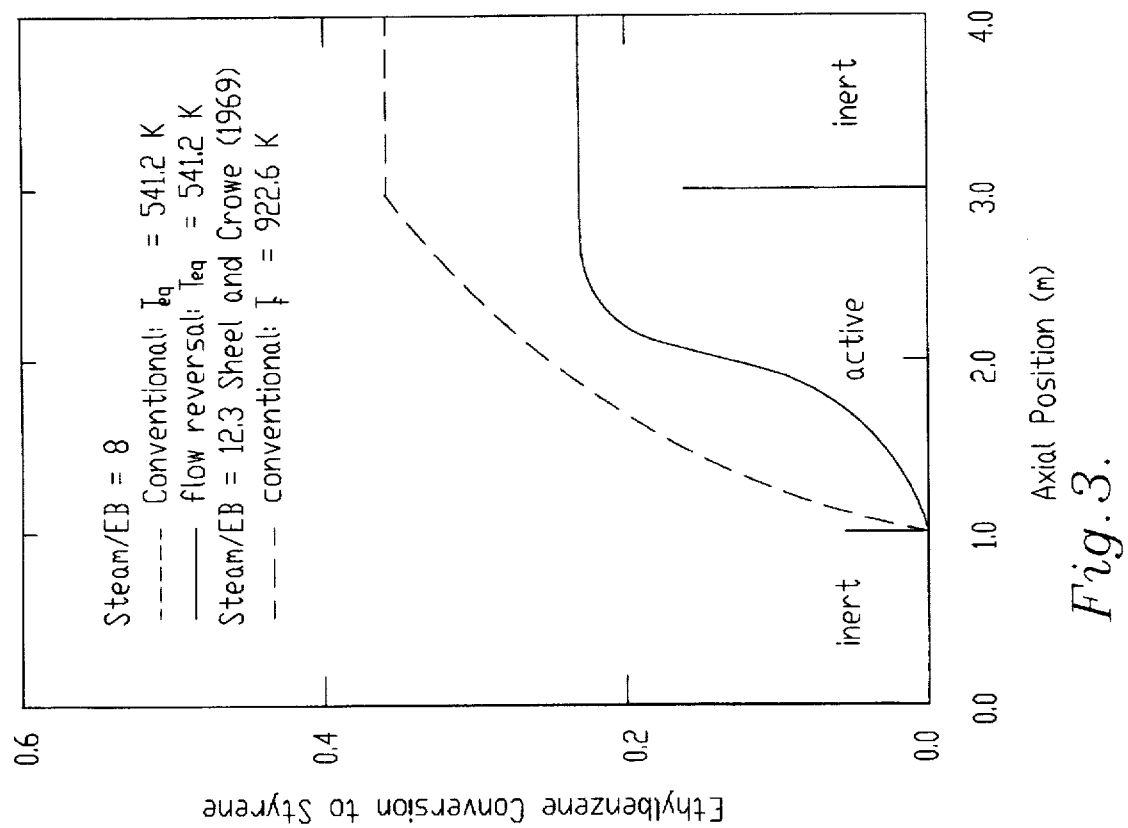
FIG. 3 is a comparison of ethylbenzene conversion (to styrene) profiles attained during reverse flow operation to those attained during conventional operation.

FIGS. 2 and 3 compare axial bed temperature and axial ethylbenzene conversion (to styrene) profiles for a reverse flow simulation and two unidirectional flow simulations. For the reverse flow case, steam (at 1150 K)/ethylbenzene (at 425 K) mixture at a molar ratio of 6:1 is alternated between the reactor ends, while additional steam at 1150 K is introduced midway between the reactor ends to achieve an overall molar ratio of 8:1. Despite the low equivalent mixed feed temperature $T_{eq}$ (541.2 K) for the reverse flow simulation, the stationary state temperatures (defined to mean that temperature attained after a sufficient number of flow reversals when the spatial/temporal profiles become invariant) in the central portion of the reactor surpass 900 K (FIG. 2) yielding roughly 22% ethylbenzene conversion to styrene (FIG. 3). Because of the relatively high endothermicity associated with the styrene formation reaction, the product stream exits the reverse flow reactor at average temperatures that are much lower than the equivalent mixed feed temperature.

Two cases of conventional (i.e., unidirectional flow) operation are compared with the reverse flow operation. For the first conventional case ($T_{eq}$=541.2 K), the reactants are added in identical amounts and at identical locations (i.e., at one reactor end and at the axial center), except that there is no flow reversal. As seen in FIG. 2 (541.2 K), the temperature profile is flat downstream of the central steam entry point. This is because the relatively low catalyst temperatures produce virtually no ethylbenzene conversion (FIG. 3). Hence heat effects due to reaction are negligible.

The second case of conventional operation employs a molar steam/ethylbenzene ratio of 12.3, a feed temperature of 922.6 K, and a reactor pressure of 2.3 atm—conditions similar to those used by an industrial reactor reported by Sheel and Crowe (1969). Steam mixed with ethylbenzene is added at one reactor end. Although a relatively high feed temperature is used, the ethylbenzene conversion to styrene (about 35%) is not much higher relative to reverse flow operation (about 22%) that employs a much lower mixed feed temperature of 541.2 K (FIG. 3). As shown later, the added energy is much more efficiently utilized during reverse flow operation, and consequently, it is possible to obtain higher conversion and similar styrene selectivity during reverse flow operation with a slightly higher mixed feed temperature (about 640 K).

Effect of Steam Temperature on Stationary State Characteristics

Figure 4:
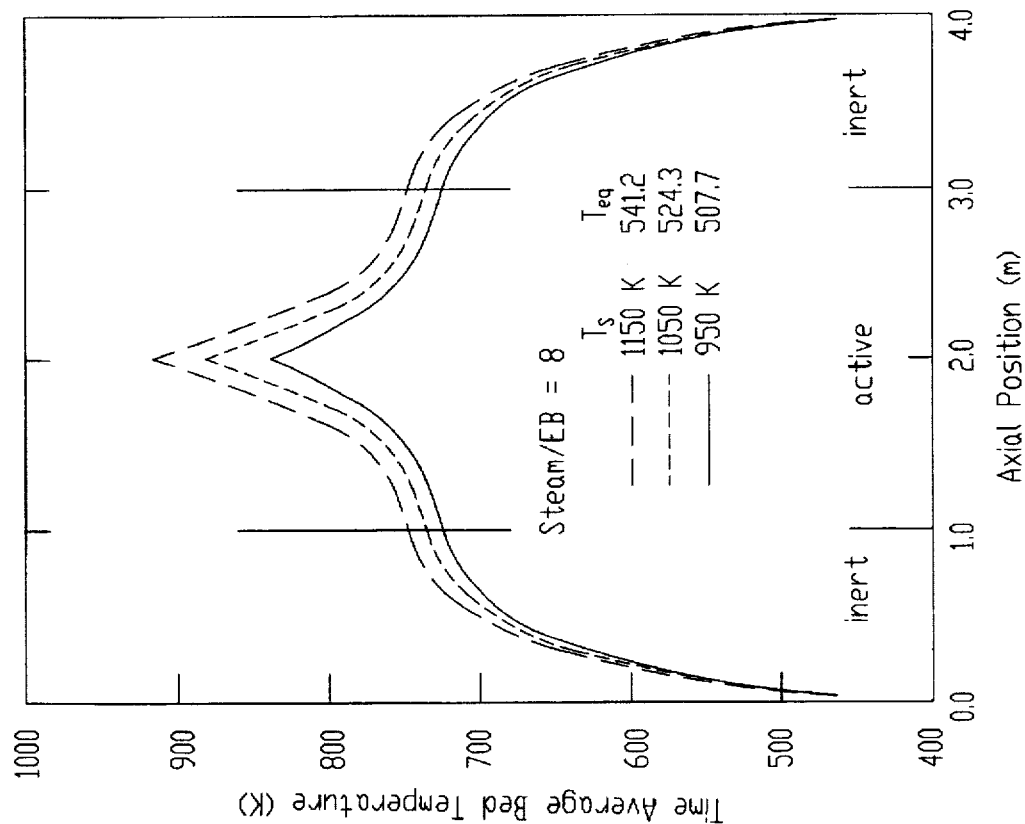
FIG. 4 is a plot showing the effect of steam temperature on time-average axial bed temperature profiles.
Figure 5:
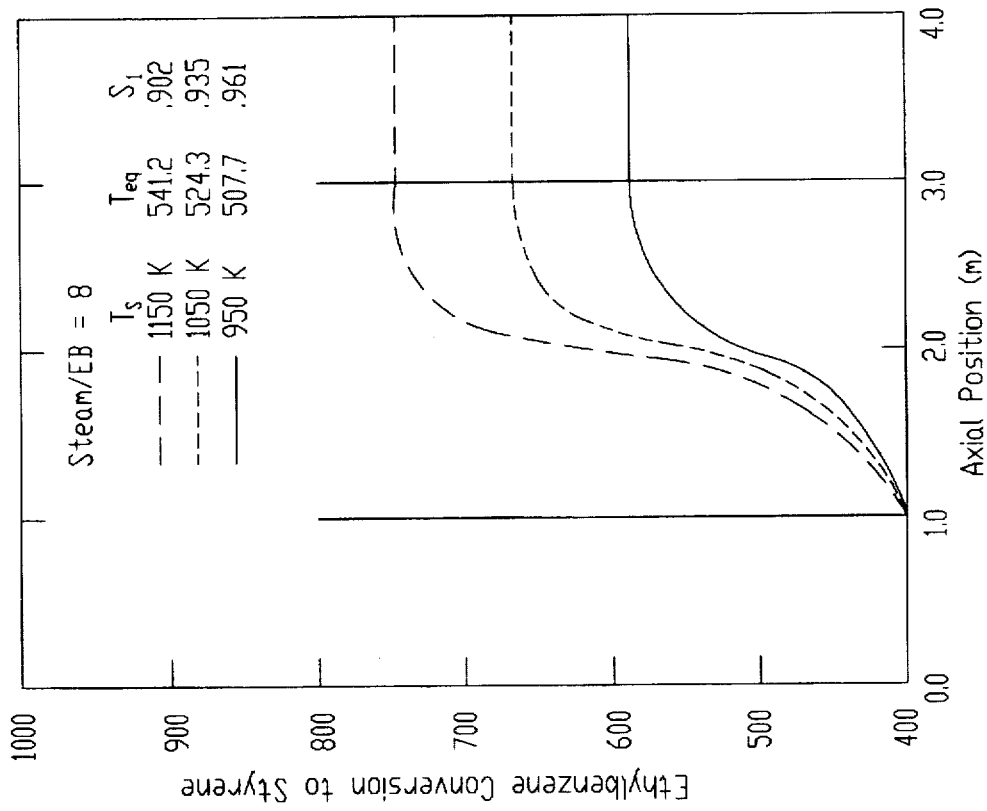
FIG. 5 is a plot showing the effect of steam temperature on axial ethylbenzene conversion (to styrene) profiles.

FIG. 4 compares time average axial catalyst temperature profiles for a reverse flow reactor in which the steam is introduced midway (2 m) between the reactor ends while ethylbenzene/steam mixture is fed from reactor ends. As inferred from FIG. 4, a 100 K increase in steam temperature yields a roughly 17 K increase in the equivalent mixed feed temperature. However, the corresponding increase in the peak temperature is approximately 42 K. Also, the average bed temperatures at the reactor ends are close in value for the three cases. This implies that the incremental energy addition is virtually completely utilized by the reactions. As shown in FIG. 5, a 200 K increase in steam temperature leads to a roughly twofold increase in ethylbenzene conversion. These results clearly demonstrate a significant advantage of the proposed reverse flow operation.

While reverse flow operation clearly facilitates greater utilization of the added energy, higher catalyst temperatures tend to promote side reactions and are hence undesirable. As shown in Table 5, although the actual conversion to styrene increases with steam temperature, the selectivity towards styrene formation shows a decreasing trend. This indicates that axial temperature profiles must be found at which conversion and selectivity to styrene formation are optimized while maintaining the advantages of reverse flow operation.

Effect of Steam Entry Location on Stationary State Characteristics

Figure 6:
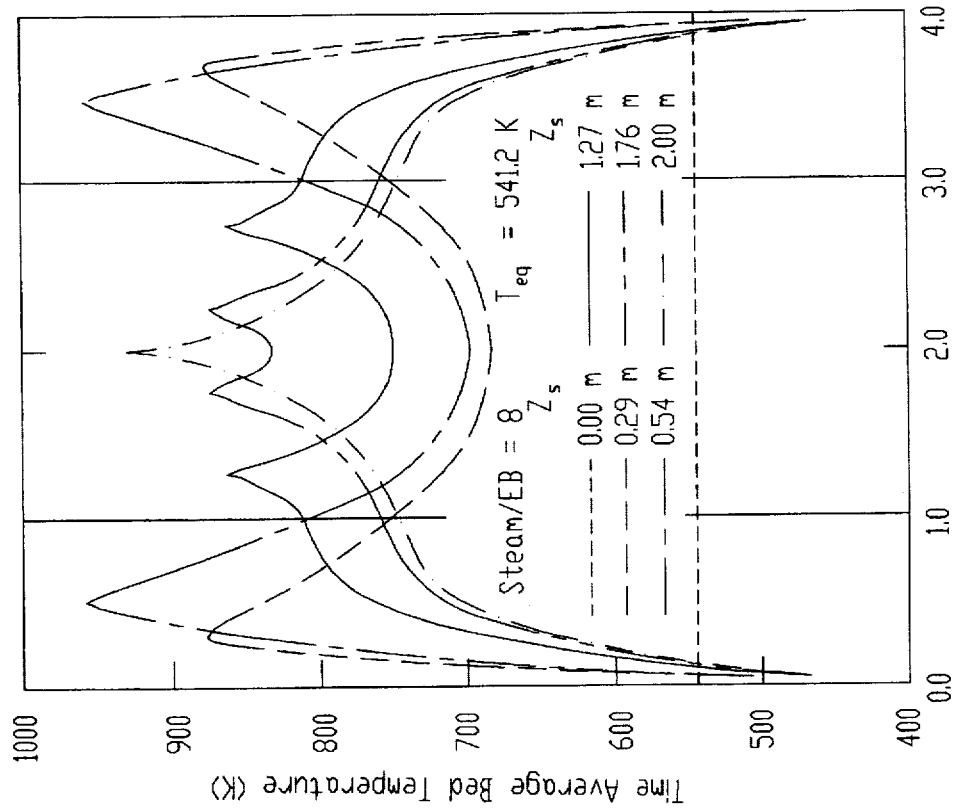
FIG. 6 is a plot showing the effect of steam entry location on time average axial bed temperature profiles.

FIG. 6 compares the time average axial bed temperature profiles when steam at 1150 K is fed at various axially symmetric locations along the reactor. FIG. 1 shows steam added across the whole cross section of the bed at $z_s$. For flow from left to right, if steam is introduced 1 m from the left end of the reactor, upon flow reversal, the gas flow would be from right to left with steam being introduced 1 m from the right end of the reactor. From FIG. 6, it can be seen that there are two steam entry locations that produce relatively higher peak temperatures than the other steam entry locations. One is at the center of the reactor ($z_s$=2 m), while the other is symmetrically located in the inert end sections ($z_s$=0.54 m).

The occurrence of a high peak temperature when the steam addition is at the axial center is to be intuitively expected because added energy must travel the farthest distance before it is convected out of the reactor. Also, whereas steam introduction at the axial center occurs over the entire flow reversal cycle, steam addition that is offset from the center occurs for only half the cycle time; during the remaining half of the cycle, steam addition is switched to the axially symmetric location. As shown in Table 2, the ethylbenzene conversion (about 0.25) is highest when steam is introduced at the center ($z_s$=2 m). In other words, the utilization of the added energy for converting ethylbenzene, which is termed the energy utilization efficiency, is maximum for steam introduction at the center. Because the enthalpy effects due to the reaction are predominantly endothermic, the space average bed temperature (798 K) is relatively lower for steam introduction at the center. For steam introduction that is slightly offset from the center but within the active section ($z_s$=1.76 m), the ethylbenzene conversion (about 0.24), and hence the energy utilization efficiency, is slightly lower. As seen from the virtual overlap of the average catalyst temperature profiles in the ethylbenzene entry regions (FIG. 6), the energy trapping in the two cases is similar. However, the decrease in the peak temperatures causes a decrease in the reaction rates and thereby in the endothermicity of the reaction, resulting in higher average bed temperatures.

Figure 7:
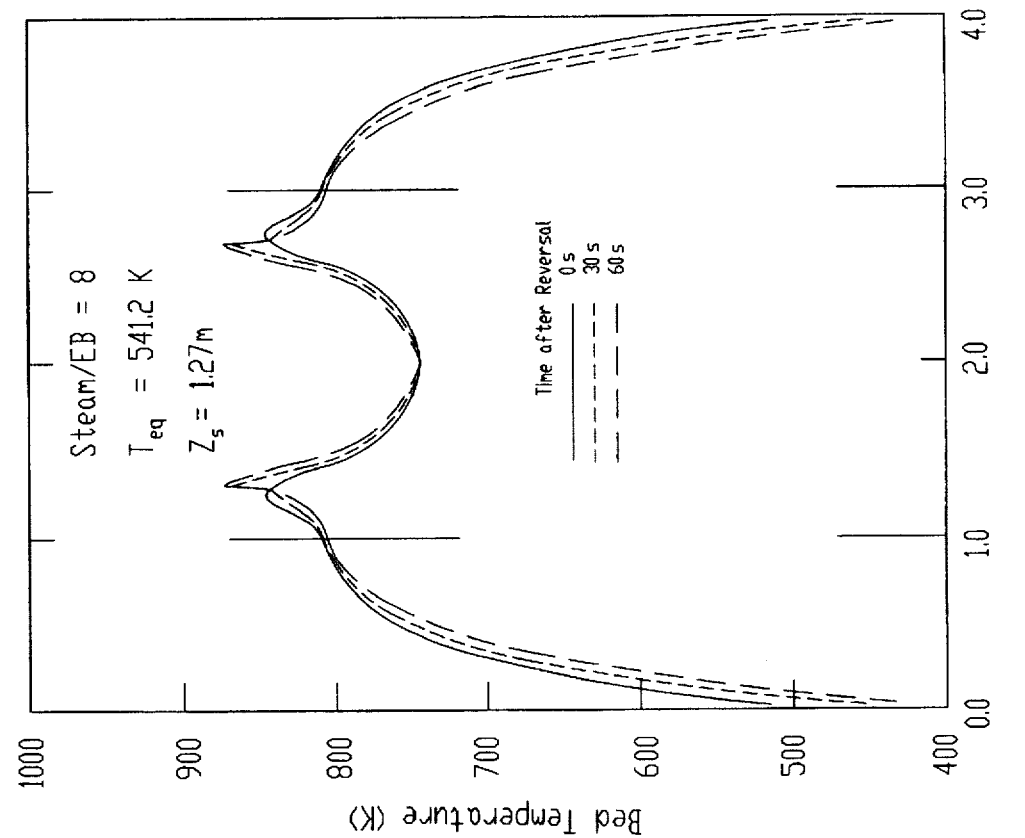
FIG. 7 is a plot showing the transient axial bed temperature profiles during a semicycle.

For steam introduction in the inert portion of the reactor ($z_s$=0.54 m) but outside the ethylbenzene entry region (where regenerative heat exchange with the cool inlet gases is the greatest), the ethylbenzene conversion is only 6% and the energy utilization efficiency is therefore quite low when compared to steam addition from the center. Because of the lower reaction rates in the active section (and hence decreased endothermic effects) and the absence of reaction in the steam entry locations, the space average and peak bed temperatures attain a maximum (Table 2). In addition to the ethylbenzene entry region, regenerative heat exchange also occurs on both sides of the two temperature peaks as they move to the right and to the left with each flow reversal. These regions are narrow as inferred from the rather small peak movement during a semicycle (FIG. 7). Consequently, the decrease in the bed temperature between the steam entry location and the center of the reactor is greater than the corresponding reaction endothermicity between these points.

For steam entry in the ethylbenzene entry region ($z_s$<0.3 m), the energy utilization efficiency decreases dramatically as the energy that is accumulated at the steam entry location during one semicycle is easily convected out the end of the bed upon flow reversal. Hence, both the peak and the space average bed temperatures decrease. Steam addition from the reactor ends mixed with the ethylbenzene feed ($T_f$=541.2 K) results in a flat temperature profile with negligible conversion. Although ethylbenzene conversion to styrene is roughly 22% for steam introduction at the center (Table 2), the selectivity toward styrene formation for steam introduction closer to the ends is higher. This again points out that there are steam entry locations between the center and the ends where both conversion and selectivity are optimized.

Effect of Inert End Section Length

Figure 8:
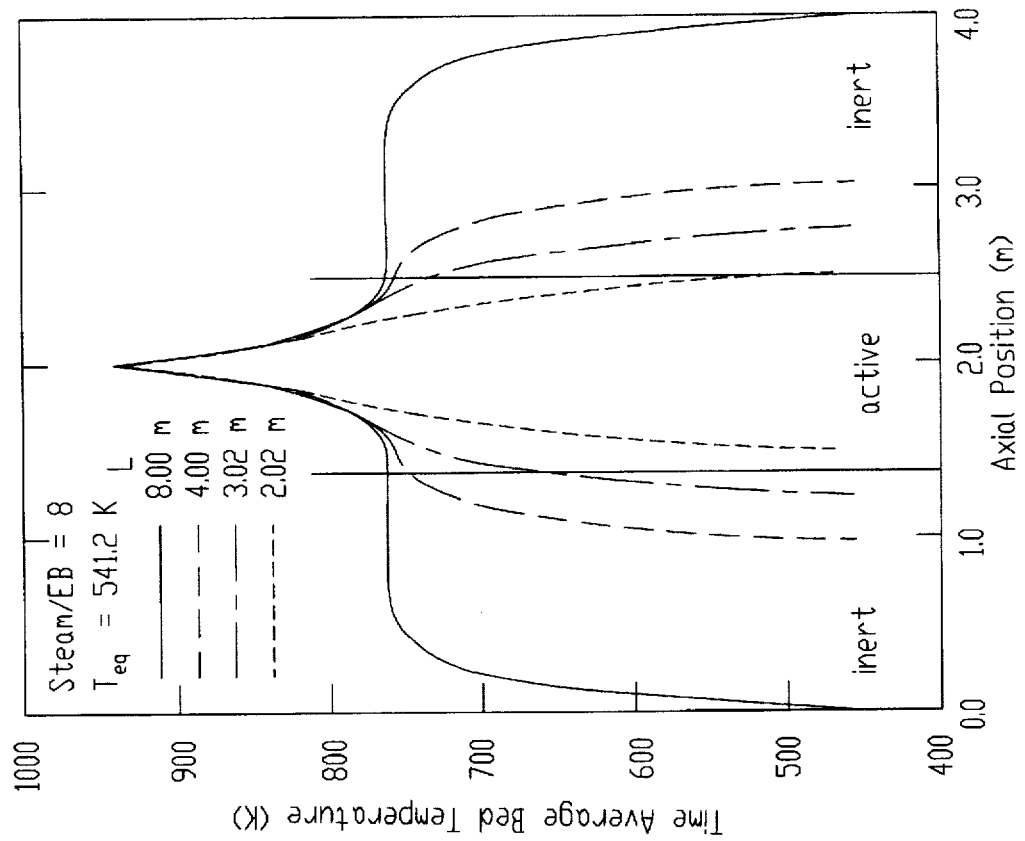
FIG. 8 is a plot showing the effect of inert bed length on time average bed temperature profiles.

FIG. 8 compares the effects of the length of the inert end section (for a constant length of active section, $L_a$=2 m) on the time average bed temperature profile (for L=8 m, $L_i$=3.5 inert, 493 axial nodes were used; for L=3.02 m, 187 nodes were used, and for L=2.02 m, 125 nodes were used). It can be seen that decreasing the length of the inert portion of the reactor decreases the amount of energy trapped in the active portion. The corresponding decreases in the space average temperatures, provided in Table 3, are relatively small except for the case where the inert end sections are not included. It should be noted that besides offering little advantage in terms of increased energy trapping, making the inert section longer than necessary causes the overall conversion for a given semicycle period to decrease. As the length of the inert section is increased, a progressively greater fraction of the reactants fails to reach the active portion of the reactor. Conversely, more product is caused to traverse the reactor twice with each flow reversal.

The Use of Multiple Steam Entry Locations

Figure 9:
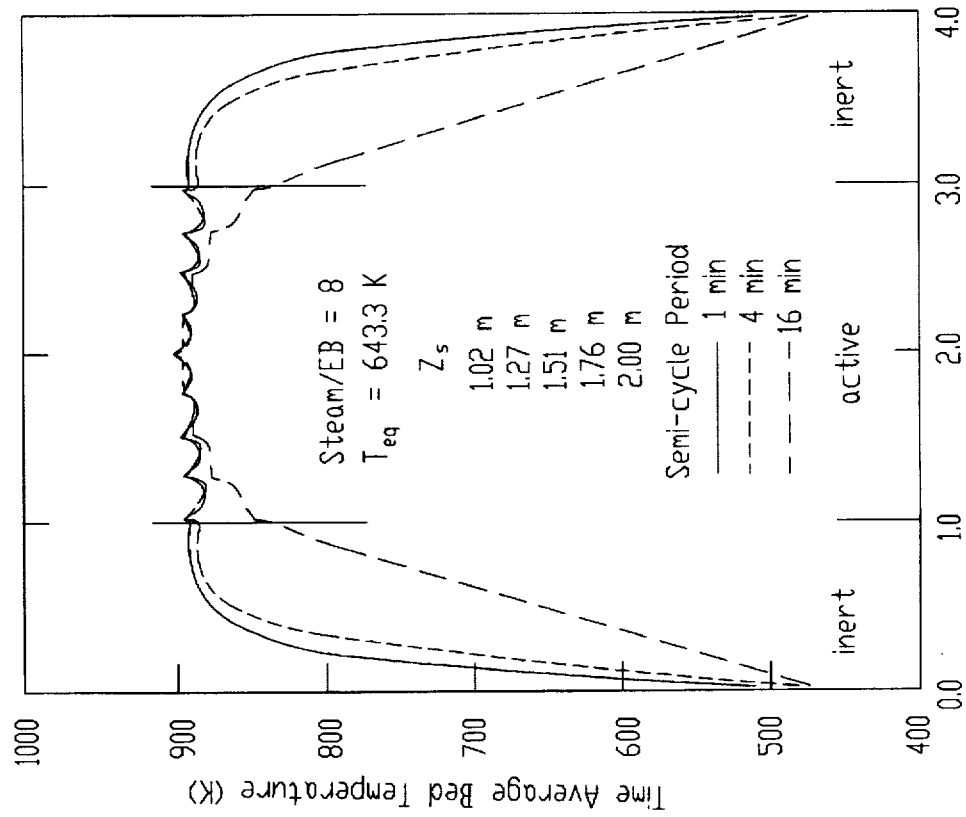
FIG. 9 is a plot showing the effect of semicycle length and multiple steam entry locations on time average axial bed temperature profiles.

It has been reported that isothermal reactor operation is desirable for optimizing ethylbenzene conversion and styrene selectivity (Short, 1985). It is shown here that more uniform catalyst temperatures can be realized through the use of multiple steam entry locations. Both the number of moles and the temperature of the steam added at the multiple axial locations are manipulated to achieve the desired temperature profile in the active section. As noted in Table 4, different flow rates of 1200 K steam are added at various axial locations such that the overall steam/ethylbenzene ration is 10.2:1 and the equivalent mixed feed temperature is 643.3 K. As seen in FIG. 9, near-isothermal catalyst bed temperatures are predicted. The results in Table 4 demonstrate that for similar ethylbenzene conversions, product selectivity and catalyst temperatures, the equivalent mixed feed temperature during reverse flow operation (643.3 K) is hundreds of degrees lower compared to conventional operation (922.6 K). These results further demonstrate the greater utilization of the added energy during reverse flow operation.

It should be noted that if the catalyst can tolerate steam/ethylbenzene ratios lower than 6:1 (i.e. without appreciable loss of catalyst activity), near-isothermal operation at about 900 K is possible with even lower overall steam addition from the reactor ends and at the interior locations. However, no published information is known to exist on the minimum amount of steam needed to maintain catalyst activity. Despite the constraint of using a minimum steam/ethylbenzene ratio of 6:1 at reactor ends, similar conversion and selectivity are predicted using equivalent mixed feed temperatures that are hundreds of degrees lower than those required during conventional operation. Thus, the feed preheating requirement is relatively low for reverse flow operation. Consequently, even with the use of external heat exchangers during conventional operation to recover some of the energy exiting the reactor, the energy efficiency of the overall process would be significantly higher in the reverse flow case.

When the semicycle period is increased to four minutes, it is seen that the resulting average temperature profile changes little. As seen from FIG. 9, the cold temperature front travels farther into the inert end sections, but the temperatures in the active section remain virtually unchanged. With a much longer period of 16 minutes, although the cold temperature front passes into the active region of the reactor, the energy trapping ability of the reverse flow reactor maintains high temperatures for a significant length of the active region. At the higher semicycle periods, it can be inferred from previous results (FIGS. 4, 6 and 8) that uniform temperatures may be maintained by either using longer inert end sections or increasing the amount of energy introduced at those steam entry locations closer to the end sections. Decreasing the semicycle period to excessively short times has an effect that is qualitatively similar to using excessively long end sections; the overall conversion would decrease as a greater fraction of the reactants fails to reach the active portion of the reactor.

Conclusions

By adding energy at interior reactor locations away from the ends, it is shown by numerical simulation that the advantages associated with periodic reverse flow operation for slightly exothermic reactions may be also realized for highly endothermic reactions, such as the catalytic dehydrogenation of ethylbenzene on a Shell-105 catalyst. In the proposed reverse flow scheme of the instant invention, a steam/ethylbenzene mixture is introduced at one reactor end while additional steam is introduced concurrently at one or more downstream location(s). The flow direction of the streams is periodically reversed by alternating the ethylbenzene/steam feed between the reactor ends and the steam introduction between axially symmetric positions. The catalyst bed is flanked by inert end sections which serve as the regenerative heat exchange medium and also prevent the occurrence of the reverse reactions at the cooler reactor ends.

Employing steam/ethylbenzene ratios of 8:1 to 10.2:1 (as compared to 12:1 to 17:1 employed during conventional adiabatic operation), it is shown that the proposed reverse flow strategy produces stationary state catalyst bed temperatures that are hundreds of degrees higher than the mixing cup temperature of the feed streams. Furthermore, because of regenerative heat exchange in the reactor entry and exit regions, the average outlet temperature is hundreds of degrees lower as compared to conventional operation. Although greater energy utilization is achieved at higher steam temperatures and for steam entry at the axial center of the reactor, undesirable side reactions can become significant at these operating conditions. Hence, steam temperatures and introduction locations must be found at which energy utilization, overall conversion and selectivity are optimized. As an example of such an optimization, it is shown that splitting the steam introduction among multiple axially symmetric locations produce near-isothermal bed temperatures that are conducive to providing desirable overall ethylbenzene conversion and styrene selectivity. Based on the results presented here, it should be possible to efficiently achieve regenerative heat exchange and energy trapping for endothermic reactions in general, employing a single reactor bed.

EXAMPLE 2

Description of Experimental Setup

Figure 10:
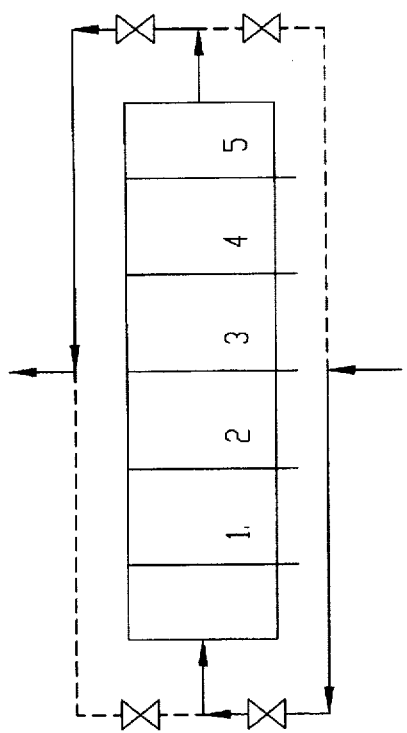
FIG. 10 is a schematic of an experimental heat exchanger with energy supplied at interior axial locations using electrical heating elements.

The experimental setup, as shown in FIG. 10, consists of an insulated stainless steel tube packed with roughly ⅛ inch γ-$Al_2O_3$ pellets. Air is introduced at one end of the 1 m long tube while energy is introduced from one or more electrical heating elements placed within the packed-bed at several axial locations. The direction of air flow is periodically reversed by alternating air introduction between the ends of the reactor while energy introduction is alternated between axially symmetric positions. A profile thermocouple measures the bed temperatures along the axis of the packed tube.

Results and Discussion

At stationary state, there is no net accumulation of energy. Thus, the same amount of energy introduced during a semicycle must also exit the heat exchanger via either the ends or the walls. Energy can transfer from the energy introduction location to the exchanger ends and eventually out of the ends either by convection (i.e. flow) or by effective conduction. A greater volume of air passing through the exchanger during a semicycle favors heat transfer by convection. Steeper temperature gradients along the axis of the heat exchanger favors heat transfer by effective conduction. Higher temperature differences between the fixed-bed heat exchanger and the surroundings favor heat loss through the walls.

Figure 11:
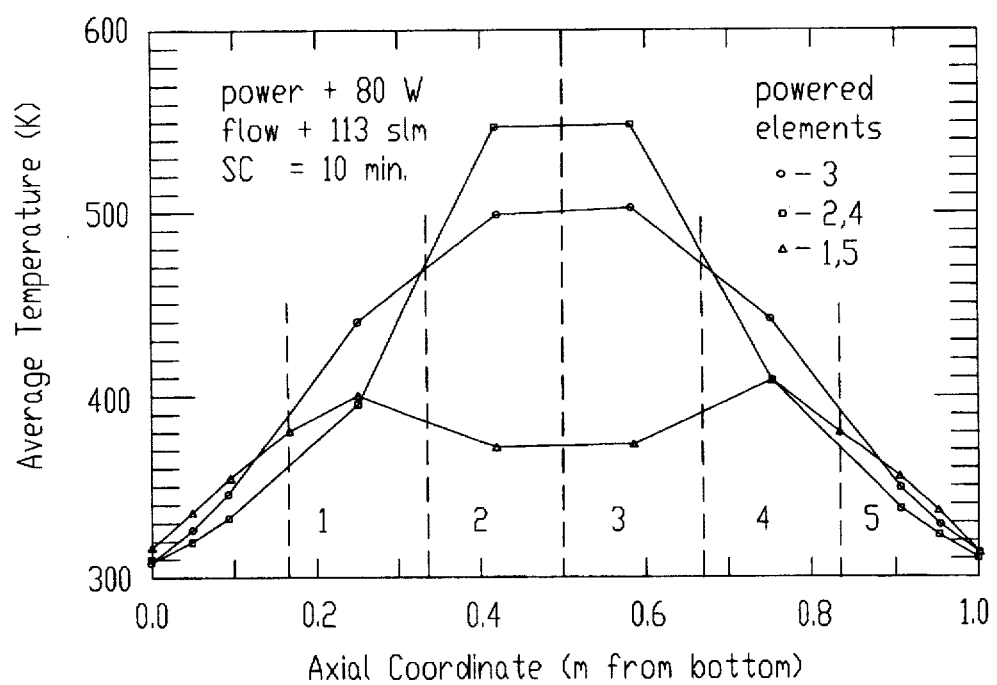
FIG. 11 is a plot showing the effect of energy introduction location on average bed temperatures.

FIG. 11 compares time average bed temperature profiles along the bed for variations in energy introduction locations. For example, when flow is from left to right, heating element 1 or 2 is turned on until the flow direction is reversed, when the energy introduction is switched to element 5 or 4, respectively. As seen in FIG. 11, energy introduced at the center has the farthest distance to travel (whether by convection or by effective conduction) before it is convected out the ends. It should be noted that there is no temperature probe at the center of the heat exchanger. For energy introduction from the center, the maximum temperature is estimated to be roughly 650 K by extrapolation.

Figure 12:
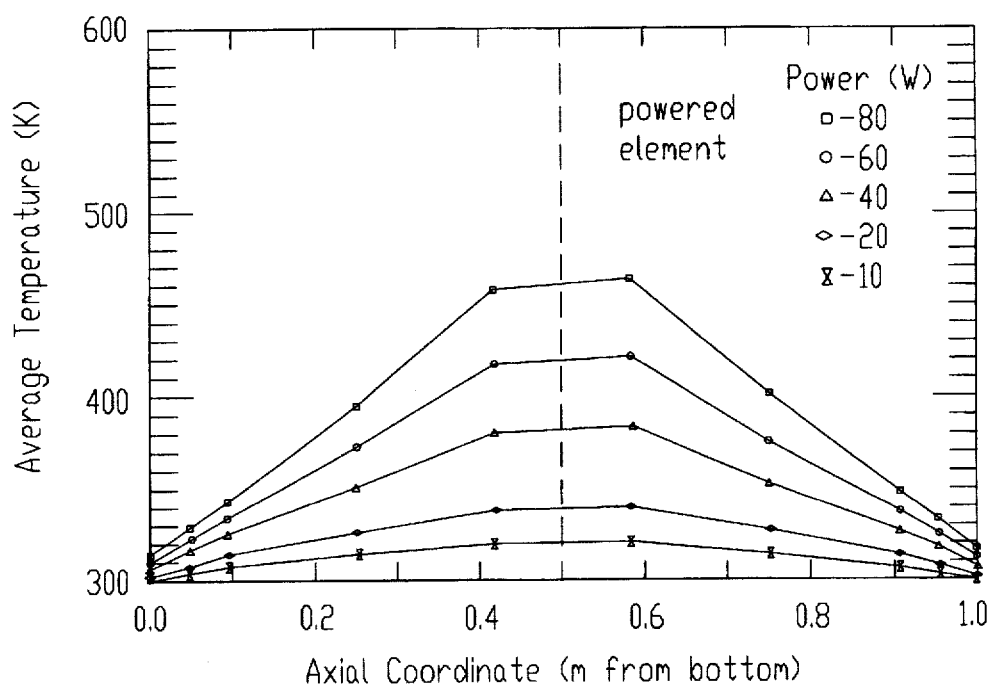
FIG. 12 is a plot showing the effect of power input on average bed temperatures.

FIG. 12 compares cycle average temperature profiles for power input variations during energy introduction at the center. It is seen that energy trapping is proportional to the power. An eight-fold increase in power results in temperature rises increasing from roughly 20 K to roughly 160 K. This is an important result because it shows that there is not a minimum power level to effect energy trapping.

Figure 13:
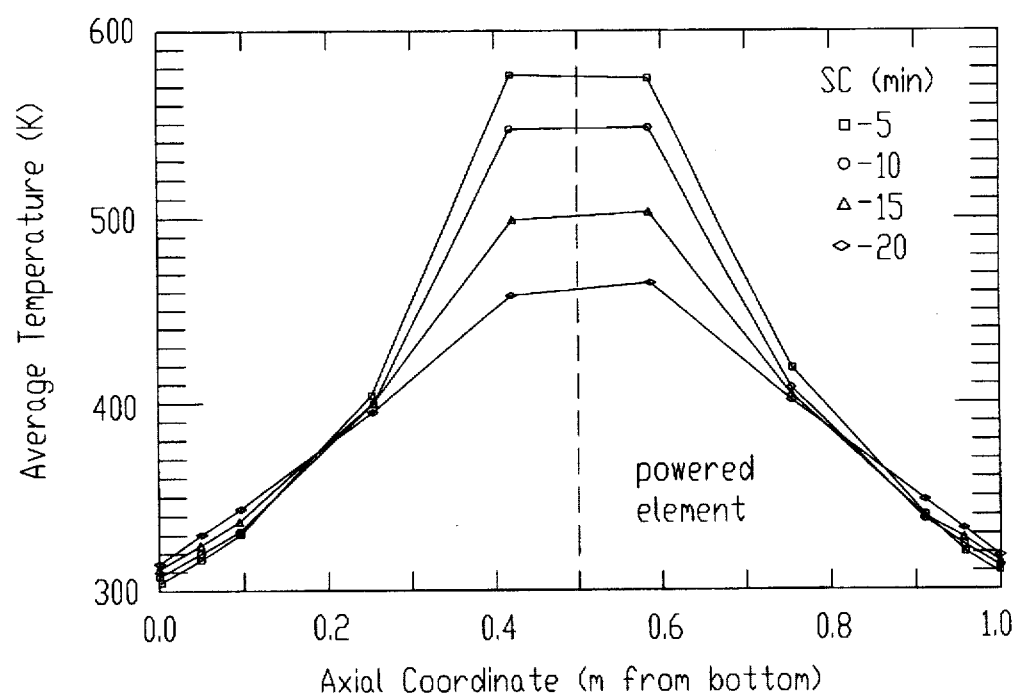
FIG. 13 is a plot showing the effect of semicycle period on average bed temperatures.

FIG. 13 compares cycle average temperature profiles for variations in the semicycle period during energy introduction at the center. As seen in FIG. 13, more energy is trapped as the semicycle period is decreased. The longer the semicycle, the farther along the exchanger a temperature profile travels. Thus, a greater portion of the axial movement of heat is caused by convection (flow). As the semicycle period decreases, the temperature profile travels a shorter distance between reversals. Thus, the axial transfer of heat due to convection is relatively less. To compensate for this decrease in transfer by convection, the temperature profile must become steeper to increase transfer by conduction. Steeper temperature gradients imply higher maximum temperatures. At sufficiently short semicycles, such that virtually all axial heat transfer is caused by conduction, the average temperature profile converges on a single solution and the peak temperature reaches a maximum.

Figure 14:
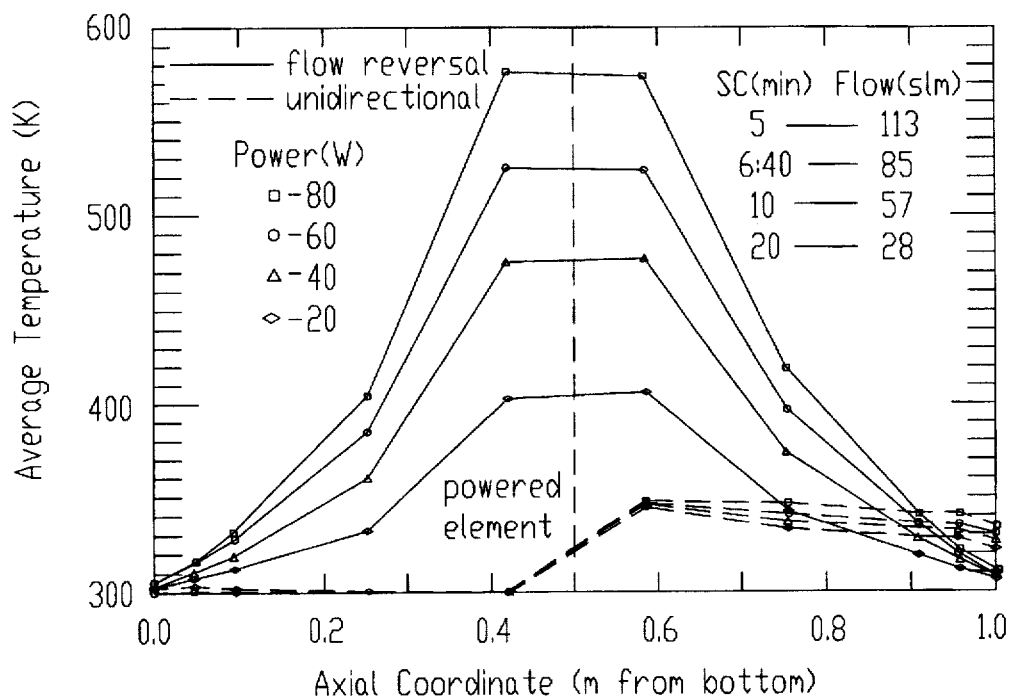
FIG. 14 is a plot showing the comparison of unidirectional and reverse flow operations.

FIG. 14 compares reverse flow operation with unidirectional operation at four flow rates. In all cases, the amount of energy input per volume of air introduced is the same. For unidirectional flow, the profiles have roughly the same maximum temperature. These profiles decrease near the exit due to heat loss through the walls. Because of longer residence times at the lower flow rates, energy loss through the walls is somewhat higher and temperatures are correspondingly lower.

For reverse flow operation, it is clearly seen from FIG. 14 that energy trapping increases with an increase in the flow rate. Since the ratio of the semicycle period to the flow rate is nearly identical for each case, the axial peak movement during a semicycle is the same. Although the energy input per volume of air is the same, the actual amount of energy introduced per unit time increases at the higher flow rates. Thus, at higher air flow rates, a correspondingly greater portion of energy must be lost through the walls at stationary state. In other words, bed temperatures are correspondingly higher for greater energy introduction rates.

FIGS. 11–14 show that bed temperatures at various axial locations along a packed tube or, equivalently, along a fixed bed reactor can be easily manipulated by suitable choice of operating parameters such as energy introduction locations, power levels, semicycle periods (and through extrapolation, by flow rates and reactor length). Such results are essential to the rational operation and control of reverse flow reactors for reactions requiring external heat transfer.

The instant invention is generally applicable to any process which carries out an endothermic reaction, or which otherwise requires heat input. Stated another way, for any process requiring heat for which a continuous, steady state, unidirectional temperature profile is known or described, the instant invention may be used to achieve the temperature profile while using significantly less heat. The invention achieves this result by employing periodic reverse flow with heat introduction at discrete reactor locations.

| Notations | |
|---|---|
| a | catalyst external surface area per unit volume, $m^{-1}$ |
| c | total molar concentration of gas phase, mol $m^{-3}$ |
| cp, g | molar heat capacity of gas phase, J $mol^{-1}$ $K^{-1}$ |
| $c_{p,i}$ | pure component molar heat capacity of specie i, J $mol^{-1}$ $K^{-1}$ |
| $c_{p,p,c}$ | heat capacity of catalyst pellets, $kg^{-1}$ $K^{-1}$ |
| $c_{p,p,i}$ | mass heat capacity of inert pellets, J $kg^{-1}$ $K^{-1}$ |
| $D_{az}$ | effective axial mass diffusivity, $m^2$ $^{-1}$ |
| $G_f$ | molar flux due to reactor feed stream, mol $m^{-2}$ $^{-1}$ |
| $G_T$ | total molar flux at an axial reactor location, mol $m^{-2}$ $s^{-1}$ |
| $\Delta H_{R,j}$ | heat of reaction for reaction j, J $mol^{-1}$ |
| $h_g$ | gas enthalpy, J $mole^{-1}$ |
| $h_h$ | external heat transfer coefficient, J $m^{-2}$ $s^{-1}$ $K^{-1}$ |
| $h_i$ | pure component gas enthalpy of specie i, J $mole^{-1}$ |
| $K_1$ | equilibrium constant, $kPa^{-1/2}$ |
| $K_{az}$ | effective axial thermal conductivity constant, J m $mol^{-1}$ $K^{-1}$ |
| L | total length of reactor bed, m (inert and active) |
| $L_i$ | length of inert catalyst bed |
| $L_a$ | length of active catalyst bed |
| P | pressure, kpa |
| $P_i$ | partial pressure of specie i, kpa |
| $Q_m$ | Energy dispersion due to mole fraction gradient, J $m^{-3}$ $s^{-1}$ |
| $Q_T$ | Energy dispersion due to temperature gradient, J $m^{-3}$ $s^{-1}$ |
| Pr | Prandtl number, dimensionless |
| $R_g$ | gas constant, J $mol^{-1}$ $K^{-1}$ |
| $R_i$ | rate of formation of specie i, mol $m^{-3}$ $s^{-1}$ |
| $r_j$ | rate for reaction j, mol $m^{-3}$ $s^{-1}$ |
| $r_p$ | pellet radius, m |
| $s_1$ | temporal average selectivity to styrene, dimensionless |
| $T_a$ | space average active section temperature at stationary state, K |
| $T_b$ | space average bed temperature at stationary state, K |
| $T_{BB}$ | feed ethylbenzene temperature, K |
| $T_{eq}$ | equivalent mixed feed temperature, K |
| $T_f$ | mixed feed temperature - unidirectional flow |
| $T_g$ | gas temperature, K |
| $T_{max}$ | maximum bed temperature at stationary state, K |
| $T_p$ | pellet temperature, K |
| $T_s$ | feed stream temperature, K |
| t | time |
| $x_j$ | temporal average conversion by reaction j, dimensionless |
| $y_i$ | mole fraction of specie i, dimensionless |
| z | axial coordinate, m |
| $z_s$ | steam entry location, m |
| Greek letters | |
| $\epsilon$ | bed void fraction |
| $\mu$ | viscosity, kg $m^{-1}$ $s^{-1}$ |
| $\rho_{p,c}$ | catalyst pellet density kg $m^{-3}$ |
| $\rho_{p,i}$ | inert pellet density kg $m^{-3}$ |
| $\Psi$ | pellet shape factor (.91 for cylindrical pellets) |
| Subscripts | |
| f | feed conditions |

APPENDIX A

Kinetic Rate Expressions

The rate equations for ethylbenzene dehydrogenation over a Shell-105 catalyst are taken from Sheel and Crowe (1969) who obtained their data from an industrial reactor. Our model neglects the correlated side reactions involving steam.

| | | | |
|---|---|---|---|
| $C_6H_5C_2H_5$ | | = $C_6H_5CHCH_2$ | + $H_2$ |
| ethylbenzene (1) | | styrene (2) | hydrogen (3) |
| $C_6H_5C_2H_5$ | | = $C_6H_6$ | + $C_2H_4$ |
| ethylbenzene (1) | | benzene (4a) | ethylene (4b) |
| $C_6H_5C_2H_5$ | + $H_2$ | = $C_6H_5CH_3$ | + $CH_4$ |
| ethylbenzene (1) | hydrogen (3) | toluene (5a) | methane (5b) |

The temperature dependence of the heat capacities and enthalpies for the various components, needed for expressing the heats of reaction and the reaction equilibrium constant as functions of temperature, were estimated from Walas (1985).

The resulting rate expressions for the formation of styrene, benzene and toluene respectively are as follows:

$$r_1 = \rho_{p,c}(1-\epsilon)\exp\left(8.1033 - \frac{21,708}{R_g \cdot T_c}\right)\left(P_1 - \frac{P_2 \cdot P_3}{K_1}\right)\frac{1}{3,600} \quad (mol\ m^{-3}\ s^{-1}) \quad (A.1)$$

$$r_2 = \rho_{p,c}(1-\epsilon)\exp\left(13.2392 - \frac{49,675}{R_g \cdot T_c}\right) P_1 \ (mol\ m^{-3}\ s^{-1}) \quad (A.2)$$

$$r_3 = \rho_{p,c}(1-\epsilon)\exp\left(0.2961 - \frac{21,857}{R_g \cdot T_c}\right) P_1 \cdot P_3 \ (mol\ m^{-3}\ s^{-1}) \quad (A.3)$$

Upon substitution of the known parameters, these equations simplify as follows:

$$r_1 = 1,306,756\exp\left(\frac{-10,925.01}{T_c}\right)\left(y_1 - \frac{1.2 \cdot y_2 \cdot y_3}{K_1}\right) (mol\ m^{-3}\ s^{-1}) \quad (A.4)$$

$$r_2 = 0.7998159 \times 10^{12} \exp\left(\frac{-25,000}{T_c}\right) y_1 \ (mol\ m^{-3}\ s^{-1}) \quad (A.5)$$

$$r_3 = 2,296,437 \exp\left(\frac{-11,000}{T_c}\right) y_1 \cdot y_3 \ (mol\ m^{-3}\ s^{-1}) \quad (A.6)$$

The rate constants in Eqs. (A.1–A.6) are evaluated at 0.1 K increments, and are similarly accessed as arrays with parameters that are proportional to the catalyst temperature.

APPENDIX B

Relationship Between Axial Mass Diffusivity and Axial Thermal Conductivity

Experimental data on the effective axial thermal conductivity for gas flow in fixed beds are sparse. Vortruba et al. (1972) reported the results of experimental conductivity measurements for air, nitrogen, and oxygen (which have similar physical properties) using a wide range of pellet sizes and pellet materials such as glass, iron and duracryl. Using an experimental procedure which involved steady state temperature measurements upstream of a heat source, Vortruba et al. (1972) provided a correlation relating the Peclet number for axial heat dispersion to the pellet size, the Reynolds number, the Prandtl number, the stagnant bed conductivity, and the intrinsic gas Diffusivity. Data were provided in the form of a plot of the Peclet number for axial heat dispersion vs. the Reynolds number. A readily discernible mathematical relationship between these dimensionless groups was not evident.

To gain insight into the dependence of the effective thermal conductivity on the various physical and operating parameters, approximately 100 of the data points from the graph presented in the referenced paper (Vortruba et al., 1972) were digitized and the axial thermal conductivity vs. the flow rate was replotted by rearranging the appropriate terms from the ordinate and abscissa. The result was a line that showed no dependence on the pellet size, and at most, questionable dependence on the pellet material over the entire range of lower rates which varied by three orders of magnitude. This is not inconsistent with experimental results by Krupiczka (1966) which show that the stagnant bed conductivity is orders of magnitude less than the effective conductivity during flow. Thus, the effective conductivity term used in the model was formulated to make it proportional to the molar gas flow rate.

The energy flux due to axial conduction is given as:

$$Q_T = \frac{\partial}{\partial z}\left(k'_{\alpha}\cdot G_T\frac{\partial T_g}{\partial z}\right) \quad (B.3)$$

The initial version of our energy balance did not account for axial energy dispersion caused by axial mass dispersion of components with different enthalpies. Consequently, for steam addition to a central node and ethylbenzene addition from the ends, both at the same temperature, a temperature increase originating at the first node upstream of the steam entry location was noted. This was caused by the diffusion of steam upstream of the steam entry point. According to the original formulation, energy based on one gas composition flowed into a differential volume, while energy based on a second gas composition flowed out of the same differential volume. Consequently, the energy balance around the differential volume upstream of the steam entry point yielded an accumulation of energy. Thus, an additional term was needed to account for the flux of energy due to the enthalpy differences of the diffusing species. As this energy flux is caused by mole fraction gradients rather than temperature gradients, this term cannot be accounted for by a term using temperature gradients. The energy balance was thus assigned an additional energy dispersion term ($Q_m$), arising out of the mass dispersion of species.

$$Q_m = \frac{\partial}{\partial z}\left(r_p \cdot G_T\frac{\partial h_g}{\partial z}\right) \quad (B.4)$$

It should be noted that whereas equation (B.4) incorporates a heat capacity dependence, equation (B.3) does not.

APPENDIX C

Second Derivative Approximation at the Steam Entry Location

At nodes other than the point of steam entry, terms containing second derivatives are expanded, then calculated using the usual centered-in-space finite difference approximations. However, steam addition at an internal node causes a discontinuity in the molar flow rate. Hence, terms containing second derivatives in the material and energy balance equations at the steam entry node had to be approximated differently based on the fluxes to the right and to the left of the steam entry location. For example, if 'i' represents the steam entry node, the axial thermal dispersion flux in Eq. (3) is written as:

$$\frac{\partial}{\partial z}\left(k'_{\alpha}\cdot G_T\frac{\partial T_g}{\partial z}\right) = k'_{\alpha}\left(\frac{G_{T,i+1}+G_{T,i}}{2}\cdot\frac{T_{g,i+1}-T_{g,i}}{\Delta z} - \frac{G_{T,i}-G_{f,steam}+G_{T,i-1}}{2}\cdot\frac{T_{g,i}-T_{g,i-1}}{\Delta z}\right)/\Delta z \quad (C.1)$$

TABLE 1

Physicochemical and Operating Parameters Used in the Simulations

| Parameter | Value | Reference |
|---|---|---|
| Surface area per unit volume, a | 1734 m$^{-1}$ | 1 |
| Pellet dimensions (cylindrical) | 0.016M × 0.0032 m | 1 |
| Void fraction, e | 0.4 | 2 |
| Catalyst effective radius, $r_p$ | 0.0025 m | 1 |
| Catalyst pellet density, $r_c$ | 2137 kg$^{-3}$ | 2 |
| Catalyst heat capacity, $c_{p,c}$ | 1047 J kg$^{-1}$ K$^{-1}$ | 3 |
| Axial thermal conductivity, K$_{az}$ | 0.44 J m mol$^{-1}$ K$^{-1}$ | 4 |
| Inert pellet density, $r_s$ | 2645 kg m$^{-3}$ | 5 |
| Inert section heat capacity, $c_{p,s}$ | 960 kg$^{-1}$ K$^{-1}$ | 5 |
| Prandtl number, Pr | 1.0 | 6 |
| Pellet shape factor, y | 0.91 | 7 |
| Ethylbenzene flow rate, $G_{EB}$ | 3.44 mol m$^2$ s$^{-1}$ | 8 |
| Length of active reactor section | 1 m | 9 |
| Steam Temperature, T$_s$ | 1150 K | 9 |
| Ethylbenzene temperature | 425 K | 9 |
| Steam/Ethylbenzene molar ratio | *:1 (6:1 at reactor end) | 9 |
| Semicycle period | 1 min. | 9 |
| Pressure, P | 2.3 atm | 1 |
| Viscosity, m | 250 kg m$^{-1}$ s$^{-1}$ | 10 |

1 - Sheel and Crowe (1969)
2 - Rase (1990)
2 - Stull (1960); for Fe$_2$O$_3$ at 980 K
4 - interpolated from the data reported by Vortruba et al. (1972)
5 - Incropera and Dewitt (1985); for fire clay brick
6 - Incropera and Dewitt (1985); for steam at 900 K
7 - Bird et al. (1960)
8 - provides a superficial velocity of 0.1 m s$^{-1}$ at ethylbenzene feed conditions. Industrial reactor reported by Sheel and Crowe (1969) used an ethylbenzene flow rate of approximately 3.6 mol m$^2$ s$^{-1}$
9 - Assumed
10 - Incropera and Dewitt (1985), Gallant (1970); a typical value in temperature range of simulations

TABLE 2

Effect of Steam Entry Location on Reverse Flow Reactor Performance
*Molar steam/ethylbenzene ratio in the combined feed streams = 8:1; for every mole of ethylbenzene added at the reactor end, six moles of steam are mixed with the ethylbenzene and two moles are alternated between two axially symmetric locations as shown.

| $Z_S$ | $T_S$ | $T_{BB}$ | $T_{eq}$ | $T_{max}$ | $T_b$ | $T_a$ | $x_1$ | $x_2$ | $x_3$ | $s_1$ |
|---|---|---|---|---|---|---|---|---|---|---|
| 0.000 | 1150 | 425 | 541.2 | 541.2 | 541.2 | 541.2 | –0 | .000 | .000 | 1.000 |
| 0.293 | 1150 | 425 | 541.2 | 880.4 | 746.7 | 704.1 | 0.33 | .000 | .000 | .992 |
| 0.537 | 1150 | 425 | 541.2 | 966.3 | 784.3 | 730.2 | 0.61 | .000 | .000 | .983 |
| 0.268 | 1150 | 425 | 541.2 | 875.7 | 760.3 | 795.4 | .191 | .005 | .007 | .940 |
| 1.756 | 1150 | 425 | 541.2 | 882.6 | 745.2 | 807.5 | .223 | .007 | .010 | .926 |
| 2,0 | 1150 | 425 | 541.2 | 918.2 | 737.3 | 798.4 | .224 | .013 | .012 | .902 |

*Other parameters used in the simulations are summarized in Table 1

TABLE 3

Effect of Inert Section Length on Reverse Flow Reactor Performance.
*Molar steam/ethylbenzene ratio in the combined feed streams = 8:1; for every mole of ethylbenzene added at the reactor end, six moles of steam are mixed with the ethylbenzene and two moles are added at the axial center of the reactor.

| L | $T_S$ | $T_{BB}$ | $T_{eq}$ | $T_{max}$ | $T_b$ | $T_a$ | $x_1$ | $x_2$ | $x_3$ | $s_1$ |
|---|---|---|---|---|---|---|---|---|---|---|
| 8.00 | 1150 | 425 | 541.2 | 918.9 | 745.6 | 800.5 | .225 | .013 | .012 | .900 |
| 4.00 | 1150 | 425 | 541.2 | 918.2 | 737.3 | 798.4 | .224 | .013 | .012 | .902 |
| 3.02 | 1150 | 425 | 541.2 | 917.5 | 737.5 | 792.8 | .216 | .012 | .011 | .903 |
| 2.02 | 1150 | 425 | 541.2 | 915.6 | — | 743.1 | .161 | .011 | .008 | .893 |

*Other parameters used in the simulations are summarized in Table 1

TABLE 4

Use of Multiple Steam Entry Locations: Comparison of Reverse Flow Reactor Performance with Conventional Operation
*Molar steam/ethylbenzene ratio in the combined feed streams = 10.2:1; for every mole of ethylbenzene added at the reactor end, six moles of steam are mixed with the ethylbenzene and 4.2 moles are alternated between five axially symmetric locations as follows: 0.19, 0.245, 0.24, 0.195, and 0.13 moles team at $z_s$ = 1.024, 1.268, 1.512, and 2.0 m, respectively.

| τ | $T_S$ | $T_{BB}$ | $T_{eq}$ | $T_{max}$ | $T_b$ | $T_a$ | $x_1$ | $x_2$ | $x_3$ | $s_1$ |
|---|---|---|---|---|---|---|---|---|---|---|
| 1 | 1200 | 425 | 643.3 | 887.6 | 848.0 | 874.6 | .392 | .027 | .024 | .884 |
| 4 | 1200 | 425 | 643.3 | 887.1 | 832.0 | 874.9 | .395 | .027 | .025 | .884 |
| 16 | 1200 | 425 | 643.3 | 885.6 | 754.0 | 846.5 | .370 | .024 | .022 | .890 |

Conventional operation using conditions reported by Sheel and crowe (1969): P = 2.3 atm, Steam/EB = 12.28, $f_{EB}$ = 3.44 mol m² s⁻¹. Steam is mixed with the ethylbenzene feed and added at the reactor end.

| τ | $T_S$ | $T_{BB}$ | $T_{eq}$ | $T_{max}$ | $T_b$ | $T_a$ | $x_1$ | $x_2$ | $x_3$ | $s_1$ |
|---|---|---|---|---|---|---|---|---|---|---|
| 1 | 922.6 | 922.6 | 922.6 | 922.6 | — | 879.6 | .354 | .031 | .015 | .884 |

* Other parameters used in the simulations are summarized in Table 1

TABLE 5

Effect of Steam Temperature on Flow Reversal Operation
*Molar steam/ethylbenzene ratio in the combined feed streams = 8:1; for every mole of ethylbenzene added at the reactor end, six moles of steam are mixed with the ethylbenzene and two moles are added at the axial center of the reactor.

| $T_S$ | $T_{EB}$ | $T_{eq}$ | $T_{max}$ | $T_b$ | $T_a$ | $x_1$ | $x_2$ | $x_3$ | $S_1$ |
|---|---|---|---|---|---|---|---|---|---|
| 950  | 425 | 507.7 | 840.3 | 710.6 | 763.8 | .122 | .002 | .003 | .961 |
| 1050 | 425 | 524.3 | 882.1 | 725.1 | 782.8 | .173 | .005 | .006 | .935 |
| 1150 | 425 | 541.2 | 918.2 | 737.3 | 798.4 | .224 | .013 | .012 | .902 |

*Other parameters used in the simulations are summarized in Table 1

REFERENCES (The teachings of all references are incorporated herein by reference)

Bird, R. B., Stewart, W. E. and Lightfoot, E. N., 1960, *Transport Phenomena.* Wiley, New York.

Boreskov, G. K., Chumachenko, V. A., Matros, Yu. Sh. (editor)oreskov, G. K., Chumachenko, V. A., Matros, Yu. Sh. (editor), Bunimovich, G.A. and Oruzheinikov, A. I., 1983, *Unsteady Processes in Catalysis, Part 1,* Institute of Catalysis, SOAN SSSR, Novosibirsk.

Boreskov, G. K. and Matros, Yu. Sh., 1983, Unsteady-state performance of herterogeneous catalytic reactions. *Catal. Rev.-Sci. and Eng.* 25, 551–590.

Bruce, G. E., Peaceman, D. W., Rachford, N. N. and Rice, J. D., 1953, Calculations of unsteady-state gas flow through porous media. *Trans. AIME,* 198, 79–92.

Carra, S. and Forni, L., 1965, Kinetics of catalytic dehydrogenation of ethylbenzene to styrene. *Ind. Eng. Chem. Process Des. Dev.* 4, 281–285.

Froment, G. F., 1967, Fixed bed catalytic reactors: current design status. *Ind. Engng Chem.* 59, 18–27.

Gallant, R. W., 1970, *Physical Properties of Hydrocarbons,* Vol 2, Gulf Publ. Co., Houston, Tex.

Haynes, T. N., Georgakis, C. and Caram, H. S., 1992, The application of reverse flow reactors to endothermic reactions. *Chem. Engng. Sci.* 47, 2927–2932.

Incropera, F. P., and DeWitt, D. P., 1985, *Fundamentals of Heat and Mass Transfer,* Wiley, New York.

Krupiczka, R., 1966, Analyse de la conductivite thermique efficace des materiaux granulaires. *Chim. Ind. Genie Chim.* 95, 1393–1396.

Lee, E. H., 1973, Iron oxide catalysts for dehydrogenation of ethylbenzene in the presence of steam. *Catal. Rev.-Sci. and Eng.* 8, 285–305.

Matros, Yu. Sh., 1989, Catalytic Process under Unsteady-state conditions, *Elsevier Science Publ., Inc.,* Amsterdam.

Modell, D. J., 1972, Optimization theory and applications: optimum temperature simulation of the styrene monomer reaction, in *Chem. Engng. Computing,* Vol. 1, AIChE, New York.

Rase, H. F., 1990, *Fixed-bed Reactor Design and Diagnostics,* Butterworths, Boston.

Sheel, J. G. P., and Crowe, C. M., 1969, Simulation and optimization of an existing ethylbenzene dehydrogenation reactor, *Canadian J. of Chem. Engng* 47, 183–187.

Short, H. C., 1985, New styrene process pares production costs. *Chemical Eng* 92(17), 30–31.

Snyder, J. D., and Subramaniam, B., 1993, Numerical simulation of a periodic flow reversal reactor for sulfur dioxide oxidation. *Chem. Engng Sci.* 48, 4051–4064.

Stull, D. R., 1960, *JANAF Thermochemical Data,* The Dow Chemical Company, Midland, Mich.

Sundaram, K. L., Sardina, H., Fernandez-Baujin, J. M. and Hildreth, J. M., 1991, Styrene plant simulation and optimization. *Hydrocarbon Processing* 70, 93–97.

Vortruba, J., Hlavacek, V. and Marek, M., 1972, Packed bed axial thermal conductivity. *Chem. Engng. Sci.* 27, 1845–1851.

Walas, S. M., 1985, *Phase Equilbria in Chemical Engineering,* Butterworths, Stoneham, Mass.

Wojciechowski, J., 1980, European Patent 0037119, priority 31.3.1980.

Yoshida, F., Ramaswami, D. and Hougen, O. A., 1962, Temperatures and pressures at the surfaces of catalyst particles. *AIChE J.* 8, 5–11.

We claim:

1. A method of carrying out an endothermic reaction in a stationary reactor having a pair of symmetrically opposed catalyst containing portions presenting two opposite ends, the reaction having a desired temperature profile within the reactor associated with an optimal conversion and product selectivity, the method comprising:

passing a reaction mixture through the stationary reactor by introducing the mixture through the reactor first end;

introducing heat at a first axially discrete location within the first symmetric portion to establish a desired temperature profile;

catalyzing the endothermic reaction to produce a desired end product; and periodically reversing the flow of the reaction mixture by introducing the mixture at the second reactor end and switching the introduction of heat to a second discrete location within said second symmetrical reactor portion which is axially symmetrical to said first location, the rate of reversal being sufficient to reduce heat losses from the reactor.

2. The method of claim 1, the rate of reversal being sufficient to optimize the selectivity of and conversion to the desired end product.

3. The method of claim 1, the reaction mixture comprising steam and ethylbenzene and the desired end product being styrene.

4. The method of claim 3, the desired temperature profile being about 922 K within the reactor catalyst.

5. The method of claim 3, the steam/ethylbenzene mixture within the reactor having a molar ratio of about 8:1.

6. The method of claim 3, the catylization occuring at about 2.3 atm.

7. A method of carrying out an endothermic reaction in a stationary reactor having an active catalyst portion comprising first and second symmetric opposed portions flanked by a pair of inert reactor sections presenting two opposing outer ends, the reaction having a desired temperature profile within the reactor associated with an optimal conversion and product selectivity, the method comprising:

passing a reaction mixture through the stationary reactor by introducing the mixture through the reactor first end;

introducing heat at a first axially discrete location within the first symmetric portion to establish a desired temperature profile;

catalyzing the endothermic reaction to produce a desired end product; and periodically reversing the flow of the reaction mixture by introducing the mixture at the second reactor end and switching the introduction of heat to a second discrete location within said second symmetrical reactor portion which is axially symmetrical to said first location, the rate of reversal being sufficient to reduce heat losses from the reactor.

8. The method of claim 7, the rate of reversal being sufficient to optimize the selectivity of and conversion to the desired end product.

9. The method of claim 7, the reaction mixture comprising steam and ethylbenzene and the desired end product being styrene.

10. The method of claim 9, the desired temperature profile being about 922 K within the reactor catalyst.

11. The method of claim 9, the steam/ethylbenzene mixture within the reactor having a molar ratio of about 8:1.

12. The method of claim 9, the catalysis occuring at about 2.3 atm.

13. A method of carrying out an endothermic reaction in a stationary reactor having an active catalyst portion comprising first and second symmetric opposed portions flanked by a pair of inert reactor sections presenting two opposing outer ends, the reaction having a desired temperature profile within the reactor associated with an optimal conversion and product selectivity, the method comprising:

passing an ethylbenzene/steam reaction mixture, having a molar ratio of 6:1 and temperature of about 541 K through the stationary reactor by introducing the mixture through the reactor first end;

introducing heat in the form of steam at a first axially discrete location within the first symmetric portion of catalyst to establish a desired temperature profile, sufficient steam being added to increase the steam/ethylbenezene molar ratio to 8:1;

catalyzing ethylbenzene to produce styrene at the pressure of 2.3 atm; and periodically reversing the flow of the reaction mixture by introducing the steam/ethylbenezene mixture having a molar ratio of 6:1 at the second reactor end and switching the introduction of heat in the form of steam to a second discrete location within said second symmetrical reactor portion which is axially symmetrical to said first location, sufficient steam being added to increase the steam/ethylbenzene ratio to 8:1, the rate of reversal being in the range of 1 every 1–16 minutes.

14. A method of carrying out a catalyzed reaction of fluid reactant(s) utilizing the addition of added heat energy to produce desired reaction product(s) and comprising the steps of:

providing a reactor having a catalyst bed presenting a catalytically active section;

providing a reactant stream for passage into and through the active section of the catalyst bed;

providing two inert regenerative heat exchange sections adjacent said catalyst bed in fluid communication therewith;

directing the reactant stream into one of the inert sections for flow into the active section of the catalyst bed;

adding and maintaining sufficient heat energy in the active section of the catalyst bed at discrete locations therein to achieve catalytic reaction of the reactant and to establish a desired temperature profile for said catalyzed reaction;

allowing the reaction product produced in the active section of the catalyst bed to flow out of the reactor through another of the inert sections and to substantially prevent the occurrence of reverse reactions;

monitoring the temperature profile of the catalytic reaction in the catalyst bed; and repetitively discontinuing direction of the reactant stream into one of the inert sections and shifting the reactant stream to another of the inert sections while at the same time shifting the reaction product exiting from the catalyst bed for flow through an inert section not then serving to direct reactant into the active section of the catalyst bed, said shifting of the reactant and reaction product stream from respective inert sections to other inert sections being carried out sufficiently repetitively to maintain a desired temperature profile in the reactor and effect trapping of energy in the inert section through which reaction product is exiting from the reactor catalyst bed.

15. The method as set forth in claim 14 wherein said steps of shifting the reactant stream and the reaction product includes the step of reversing the flow of the reactant through the active section of the catalyst bed by alternately shifting the flow of the reactant between respective inert sections and in conjunction therewith alternately shifting the flow of the reaction product between a corresponding inert section not then serving to direct reactant into the active section of the catalyst bed.

16. The method as set forth in claim 14 wherein said step of introducing heat energy into the active section of the catalyst bed includes introduction of heat energy into substantially the center of the catalytically active section of the catalyst bed.

17. The method as set forth in claim 14 wherein said step of adding heat energy to the active section of the catalyst bed includes adding heat energy at a plurality of discrete locations which are axially symmetrical with respect to the axis of the bed.

18. The method as set forth in claim 14 wherein said step of adding heat energy to the active section of the catalyst bed includes adding steam to the active section of the catalyst bed.

19. The method as set forth in claim 14 wherein said step of adding heat energy to the active section of the catalyst bed includes adding electrically derived power to the active section of the catalyst bed.

20. The method as set forth in claim 14 wherein is included the steps of providing a fixed catalyst bed and inert sections located on opposite, flanking sides of the catalyst bed, said steps of shifting the reactant stream and the reaction product including the step of reversing the flow of the reactant through the active section of the catalyst bed reactant stream by alternately shifting the flow of the reactant between respective inert sections and in conjunction therewith alternately shifting the flow of the reaction product between a corresponding inert section not then serving to direct reactant into the active section of the catalyst bed.

21. The method as set forth in claim 14 wherein said reactant stream comprises a mixture of steam and ethylbenzene.

* * * * *